(12) United States Patent
Gonioukh et al.

(10) Patent No.: US 6,593,437 B1
(45) Date of Patent: Jul. 15, 2003

(54) METAL ORGANIC CATALYSTS FOR POLYMERIZING UNSATURATED COMPOUNDS

(75) Inventors: Andrei Gonioukh, Dudenhofen (DE);
Wolfgang Micklitz, Neustadt (DE);
Benno Bildstein, Innsbruck (AT);
Michael Malaun, Wenns (AT);
Andreas Hradsky, Innsbruck (AT)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 09/959,382

(22) PCT Filed: May 4, 2000

(86) PCT No.: PCT/EP00/04005

§ 371 (c)(1), (2), (4) Date: Oct. 24, 2001

(87) PCT Pub. No.: WO00/66600

PCT Pub. Date: Nov. 9, 2000

(30) Foreign Application Priority Data

May 4, 1999 (DE) .......................................... 199 20 486

(51) Int. Cl.[7] .................................................. C08F 4/70
(52) U.S. Cl. ....................... 526/117; 526/161; 526/171; 526/172; 526/169.1; 526/134; 556/137; 556/140; 556/142; 556/143
(58) Field of Search .............................. 526/161, 169.1, 526/172, 117

(56) References Cited

FOREIGN PATENT DOCUMENTS

| DE | 199 20 486 A1 | * 11/2000 | ............ C07F/17/00 |
|---|---|---|---|
| DE | 199 44 993 A1 | * 3/2001 | ............ C07F/15/04 |
| GB | 2 314 518 | 1/1998 | |
| WO | 91/09882 | 7/1991 | |
| WO | 96/23010 | 8/1996 | |
| WO | WO 01/214586 A1 | * 3/2001 | ......... C07D/207/50 |

OTHER PUBLICATIONS

Orgometallics, 1999, 4235–4336, Bildstein et al.
Chemm.Commun., 1998 849–850, Britovsek et al.
J.Am.Chem.Soc., 1998, 120, 4049–4050,Small et al.
J.Am.Chem.Soc., 1995, 117, 6414–6415, Johnson et al.
J.Am.Chem.Soc.1996, 118, 267–268,Johnson et al.
Ferrocenylamine, Herberhold et al.,81–83, 1986.
Bis(diszadien)metall(O)–Komplexe, IV . . . , Dieck et al. 823–832.
Synthesis, Bildstein et al., 158–160.
J. Org. Chem. 540 (1997) 127–145, Bildstein et al.
Organometallies, 1990,9,301–306, Knox et al.

\* cited by examiner

*Primary Examiner*—David W. Wu
*Assistant Examiner*—Rip A Lee
(74) *Attorney, Agent, or Firm*—Keil & Weinkauf

(57) ABSTRACT

A process for preparing 1,2-diimine compounds of the formula I

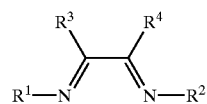

where $R^1$ and $R^2$ are, independently of one another, alkyl, aryl or metallocenyl radicals, and $R^3$, $R^4$ are, independently of one another, H, alkyl or aryl radicals or $R^3$ and $R^4$ are joined so as to form, with inclusion of the two imine carbon atoms, a 5- to 8-membered ring which may be saturated or unsaturated and may be unsubstituted or substituted by any hydrocarbon radicals. The process involves reacting 1,2-dicarbonyl compounds with primary amines, which have been activated with trialkylaluminum compounds prior to the reaction with the 1,2-dicarbonyl compounds. 1,2-Diimine compounds of the formula I in which $R^1$ and $R^2$ are, independently of one another, metallocenyl radicals can be used to prepare metal complexes which can be used as catalysts in a process for the polymerization of unsaturated compounds.

21 Claims, 5 Drawing Sheets

Figure 1:
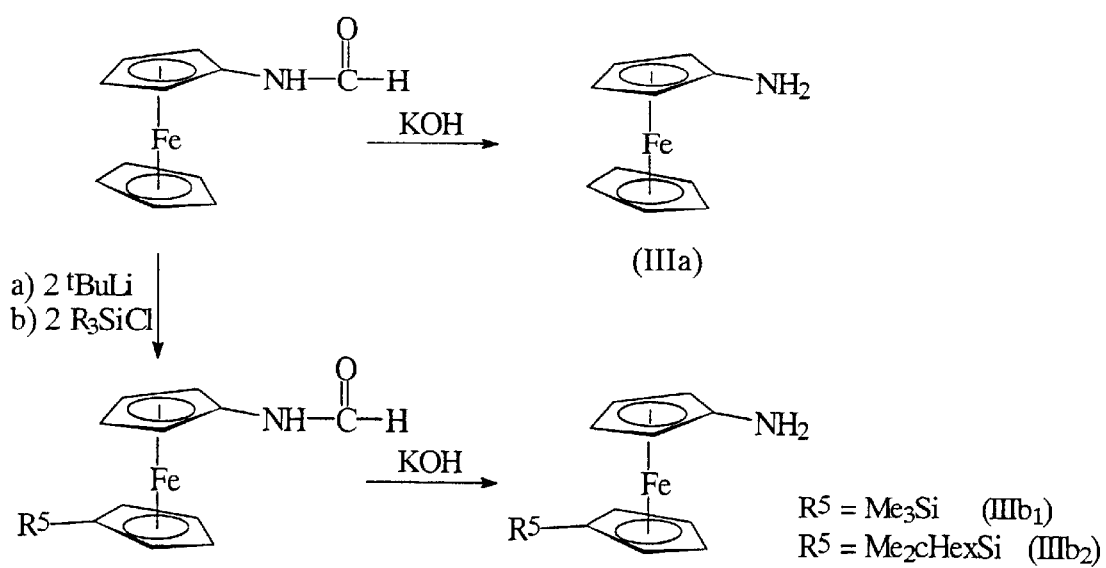

(IIIa): $R_n$ = H, n = 1
(IIIb$_1$): $R_n$ = Me$_3$Si, n = 1
(IIIb2): $R_n$ = Me$_2$cHexSi, n = 1
(IIIc): $R_n$ = Me, n = 5

(Ia'): $R_n$ = H, n = 1
(Ib$_1$'): $R_n$ = Me$_3$Si, n = 1
(Ib$_2$'): $R_n$ = Me$_2$cHexSi, n = 1
(Ic'): $R_n$ = Me, n = 5

METAL ORGANIC CATALYSTS FOR POLYMERIZING UNSATURATED COMPOUNDS

The present invention relates to a process for preparing 1,2-diimine compounds, metallocenyl-substituted 1,2-diimine compounds, catalysts having metallocenyl-substituted 1,2-diimine ligands, a process for preparing them and also their use in the polymerization of unsaturated compounds.

The use of metallocene catalysts in the polymerization of unsaturated compounds has a great influence on the preparation of polyolefins since it opens up a route to novel polyolefinic materials or to materials having improved properties. There is therefore great interest in the development of new families of catalysts for the polymerization of unsaturated compounds in order to obtain better control over the properties of polyolefins or further novel products.

The use of transition metal catalysts containing late transition metals (in particular transition metals of transition group VIII of the Periodic Table of the Elements) is of particular interest because of their ability to tolerate heteroatom functions. However, a disadvantage is that the transition metal catalysts containing late transition metals frequently tend, in contrast to transition metal catalysts containing early transition metals (in particular transition metals of transition groups III to V of the Period Table of the Elements), to result in dimerization or oligomerization of unsaturated compounds because of competing β-hydride elimination.

The prior art discloses transition metal catalysts derived from late transition metals which are suitable for the polymerization of unsaturated compounds.

V. C. Gibson et al., Chem. Commun. 1998, 849–850, and M. Brookhart et al., J. Am. Chem. Soc. 1998, 120, 4049–4050, disclose new olefin polymerization catalysts based on Fe(II) and Co(II). These catalysts bear 2,6-bis(imino)pyridyl ligands which are aryl-substituted on the imino nitrogens and display high activities in the polymerization of ethlyene. The polyethylene obtained is essentially linear and the molecular weight is strongly dependent on the substituents on the aryl radical. H. tom Dieck, Z. Naturforsch. 1981, 36b, 823–832, relates to bis(diazadiene)nickel(0) complexes having aromatic substituents on the nitrogen atom and also their conformations as a function of the substituents on the aromatic radical.

M. Brookhart et al., J. Am. Chem. Soc. 1995, 117, 6415–6415, describe catalysts based on Pd(II) and Ni(II) for the polymerization of ethylene and α-olefins. These catalysts bear 1,2-diimine ligands. In the polymerization of ethylene and α-olefins, they give polymers having a high molecular weight. The branching of polyethylene prepared using these catalysts can be adjusted from strongly branched to only slightly branched as a function of the ligand system, metal, temperature and the pressure. According to M. Brookhart et al., J. Am. Chem. Soc. 1996, 118, 267–268, the copolymerization of ethylene and propylene with functionalized vinyl monomers is also possible using these catalysts with Pd(II) as metal.

WO 96/23010 relates to processes for the polymerization and copolymerization of olefins such as ethylene, acrylic olefins and others. Catalysts used are transition metal compounds containing metals selected from the group consisting of Ti, Zr, Sc, V, Cr, rare earth metals, Se, Co, Ni and Pd. Ligand systems disclosed are diimine ligand systems, in particular 1,2-diimine ligand systems.

It is an object of the present invention to provide a novel catalyst containing a transition metal of transition group VIII of the Periodic Table of the Elements (late transition metal) as central metal for the polymerization of unsaturated compounds. This object can be divided into the provision of a ligand system for this catalyst and a process for preparing this ligand system and provision of a process for preparing the corresponding catalyst.

We have found that this object is achieved by a process for preparing 1,2-diimine compounds of the formula I,

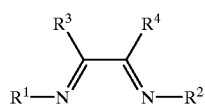

I where the symbols have the following meanings $R^1$ and $R^2$ are, independently of one another, alkyl, aryl or metallocenyl radicals, and $R^3$, $R^4$ are, independently of one another, H, alkyl or aryl radicals, or $R^3$ and $R^4$ are joined so as to form, with inclusion of the two imine carbon atoms, a 5- to 8-membered ring which may be saturated or unsaturated and may be unsubstituted or substituted by any hydrocarbon radicals, by reacting 1,2-dicarbonyl compounds with primary amines.

In the process of the present invention, the amines are activated with trialkylaluminum compounds prior to the reaction with the 1,2-dicarbonyl compounds.

The process of the present invention is particularly useful for preparing 1,2-diimine compounds having bulky radicals $R^1$ to $R^4$ which cannot be obtained without addition of trialkylaluminum compounds. Thus, the process of the present invention makes it possible to obtain new groups of 1,2-diimine compounds which can be used as ligand systems for novel catalysts.

For the purposes of the present invention, alkyl radicals $R^1$, $R^2$, $R^3$ and $R^4$ are linear, branched or cyclic alkyl radicals, preferably $C_1$–$C_{20}$-alkyl radicals, particularly preferably $C_1$–$C_8$-alkyl radicals.

Aryl radicals are, for the purposes of the present invention, unsubstituted and substituted aryl radicals, preferably $C_6$–$C_{20}$-aryl radicals, particularly preferably substituted $C_6$–$C_{14}$-aryl radicals, which may be monosubstituted or polysubstituted, very particularly preferably $C_1$–$C_6$-alkyl-substituted $C_6$–$C_{10}$-aryl radicals such as 4-methylphenyl, 2,6-dimethylphenyl, 2,6-diethylphenyl, 2,6-diisopropylphenyl, 2-tert-butylphenyl, 2,6-di(tert-butyl)phenyl or 2-i-propyl-6-methylphenyl.

According to the present invention, $R^3$ and $R^4$ in the formula I may be joined so as to form, with inclusion of the two imine carbon atoms, a 5- to 8-membered ring which may be saturated or unsaturated and may be unsubstituted or substituted by any hydrocarbon radicals.

For the purposes of the present invention, hydrocarbon radicals are linear, branched or cyclic hydrocarbon radicals which may be saturated or monounsaturated or polyunsaturated. The cyclic hydrocarbon radicals may together with the 5- to 8-membered ring system form a fused system which may be ortho-fused or ortho- and peri-fused. The hydrocarbon radicals preferably have from 1 to 20 carbon atoms. Particular preference is given to a fused-on naphtho group which may be unsubstituted or monosubstituted or polysusbstituted by alkyl radicals or aryl radicals, so that, with inclusion of the 5- to 8-membered ring system formed from $R^3$ and $R^4$, an ortho- and peri-fused system is formed.

In a fused system (at least two rings each having at least five ring atoms including the shared atoms), if two rings have two atoms in common or the system contains a plurality of rings each having two atoms in common, the system is said to be ortho-fused. The number of shared atoms is then double the number of shared sides. If a ring of a fused system shares two atoms with each of two or more rings of a series of adjacent rings, the system is said to be ortho- and peri-fused and the number of atoms is less than twice the number of the shared sides.

For the purposes of the present invention, metallocenyl radicals are bis($\eta^5$-cyclopentadienyl)metal radicals in which the metal is preferably Fe, Co$^+$, Ni, Ru, Os, Rh$^+$ or Ir$^+$. The metal is particularly preferably Fe, i.e. the metallocenyl radical is a bis($\eta^5$-cyclopentadienyl)iron radical (ferrocenyl radical). The cyclopentadienyl radicals may be substituted or unsubstituted, with the radical being bound to the imine nitrogen in the formula I via one of the two cyclopentadienyl radicals. Preferred substituents on the cyclopentadienyl radical are —Me, —SiMe$_3$ or —SicHexMe$_2$.

The process of the present invention is preferably used for preparing compounds of the formula I in which the radicals R$^1$ and R$^2$ are, independently of one another, substituted aryl radicals or metallocenyl radicals. R$^1$ and R$^2$ are particularly preferably ferrocenyl radicals. Very particular preference is given to ferrocenyl radicals of the formulae IIa, IIb and IIc,

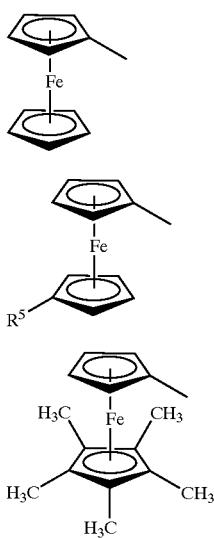

where R$^5$ is —Me, —SiMe$_3$ or —SicHexMe$_2$.

In the process of the present invention, use is made of primary amines of the formula III, $$R^1-NH_2 \text{ or } R^2-NH_2 \qquad (III),$$

where R$^1$ and R$^2$ are as defined above.

The ferrocenylamines IIIa which are particularly preferably used are prepared, in the case of unsubstituted ferrocenylamine, as described by M. Herberhold in Organometallic Synthesis 3, R. E. King and J. J. Eisch (Editors), Elsevier, Amsterdam (1986) 81–83. For this purpose, ferrocenecarboxylic acid is firstly converted into ferrocenyl azide which is reacted with acetic anhydride in a variant of the Curtius rearrangement to form N-acetylferrocenylamine (monoferrocenylacetamide). Hydrolysis of the N-acetylferrocenylamine with aqueous potassium hydroxide gives ferrocenylamine.

Silyl-substituted ferrocenylamines IIIb can be obtained by reacting N-acetylferrocenylamine with an excess of chlorosilane, for example trimethylchlorosilane or cyclohexyldimethylchlorosilane. The acetamide obtained can once again be converted into the corresponding amine by hydrolysis with aqueous potassium hydroxide. FIG. 1 shows a reaction scheme for preparing selected ferrocenylamines.

Ferrocenylamines having a pentamethylcyclopentadienyl radical IIIc can be obtained by firstly preparing 1,2,3,4,5-pentamethylferrocene-1-carboxylic acid as described by B. Bildstein et al., J. of Organomet. Chem. 540 (1997) 127–145. For this purpose, 1,2,3,4,5-pentamethylferrocene is firstly reacted with n-butyllithium and potassium tert-butoxide and subsequently with solid carbon dioxide. The carboxylic acid obtained is reacted with phosphorus pentachloride as described by Bildstein et al. to form the corresponding acid chloride. After removal of the solvent and other volatile constituents, the residue is dissolved in an organic solvent, generally in an aromatic solvent, preferably in toluene, and preferably reacted with sodium azide in the presence of a phase transfer catalyst, e.g. using benzyltriethylammonium bromide as phase transfer catalyst, to form the corresponding carboxylic acid azide. After aqueous work-up of the azide, carried out by methods known to those skilled in the art, and purification, e.g. by chromatography, the carboxylic acid azide obtained is reacted with acetic anhydride to form 1,2,3,4,5-pentamethyl-ferrocen-1-yl-acetamide. The corresponding aminoferrocene is prepared by aqueous hydrolysis of the acetamide using potassium hydroxide.

Figure 2:
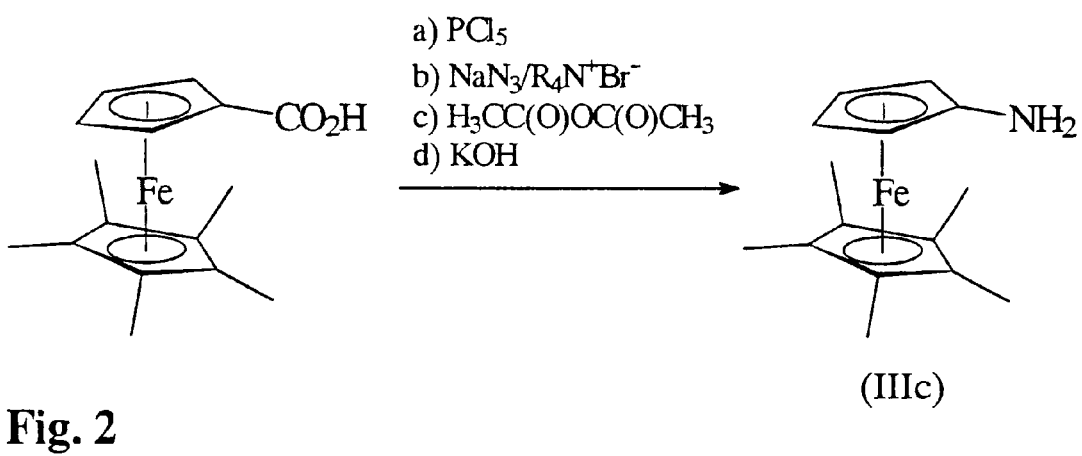

Instead of aqueous hydrolysis using potassium hydroxide, the corresponding ferrocenylacetamides can also by hydrolyzed with potassium hydroxide in an alcohol, preferably ethanol, to form the corresponding aminoferrocenes. The work-up of the aminoferrocenes is carried out in a customary manner, e.g. by extraction with diethyl ether and subsequent removal of the ether under reduced pressure. FIG. 2 shows, by way of example, the synthesis of ferrocenylamines having a pentamethyl-substituted cyclopentadienyl ring.

The 1,2-dicarbonyl compounds used in the process of the present invention are compounds of the formula IV:

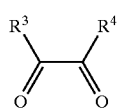

IV where R$^3$ and R$^4$ are as defined above. It is preferred that R$^3$ and R$^4$ are, independently of one another, H or C$_1$–C$_{20}$-alkyl radicals, or R$^3$ and R$^4$ are joined so as to form, with inclusion of the two carbonyl carbon atoms, a 5- to 8-membered ring which may be saturated or unsaturated and may be unsubstituted or substituted by any hydrocarbon radicals as defined above. Particular preference is given to using carbonyl compounds of the formulae IVa, IVb and IVc,

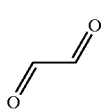

IVa

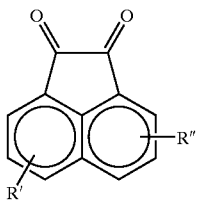 IVb

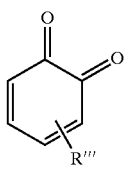 IVc where R', R'', R'''=H, alkyl or aryl.

In the process of the present invention, the primary amines are activated with trialkylaluminum compounds before they are reacted with the dicarbonyl compounds. Here, preference is given to using trialkylaluminum compounds of the formula V.

$$R^6R^7R^8Al \qquad V$$

In this formula, $R^6$, $R^7$, $R^8$ are, independently of one another, $C_1$–$C_{10}$-alkyl radicals. Particular preference is given to $R^6$, $R^7$ and $R^8$ being, independently of one another, $C_1$–$C_3$-alkyl radicals such as methyl, ethyl and i-propyl. $R^6$, $R^7$ and $R^8$ are very particularly preferably each methyl.

Reaction of a primary amine of the formula III with trialkylaluminum compounds of the formula V gives activated amines of the formula VI, $$[R^1\!-\!NH\!-\!AlR^6R^7]_n \text{ or } [R^2\!-\!NH\!-\!AlR^6R^7]_n \qquad (VI)$$

where the radicals $R^1$, $R^2$, $R^6$ and $R^7$ are as defined above and n=2 to 4. In the particularly preferred preparation of ferrocenyl-substituted 1,2-diimine compounds, the preferred reaction of the corresponding ferrocenylamine with trimethylaluminum gives activated amines of the formula VIa,

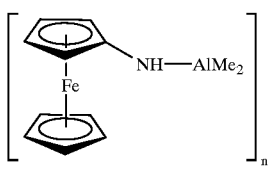 (VIa)

where n=2 to 4.

The process of the invention is generally carried out in two steps:
A preparation of the activated amine;
B reaction of the activated amine with a 1,2-dicarbonyl compound of the formula IV.

A preparation of the Activated Amine:

A primary amine of the formula III is mixed with a trialkylaluminum compound in a molar ratio of generally from 1.5:1 to 1:1.5, preferably from 1.3:1 to 1:1.3, very particularly preferably about 1:1, in a solvent. Suitable solvents are organic solvents which are preferably water-free; particular preference is given to water-free aromatic solvents, among which toluene is very particularly preferred. The reaction mixture is stirred at a temperature which depends on the reactants used and on the solvent and is generally in the range from room temperature to 110° C., preferably from 50 to 80° C., particularly preferably about 70° C. After a reaction time which generally depends on the reactants and is usually from 10 minutes to 5 hours, preferably from 1 to 4 hours, particularly preferably about 3 hours, the second step of the process of the present invention is carried out in situ without further work-up.

Figure 3:
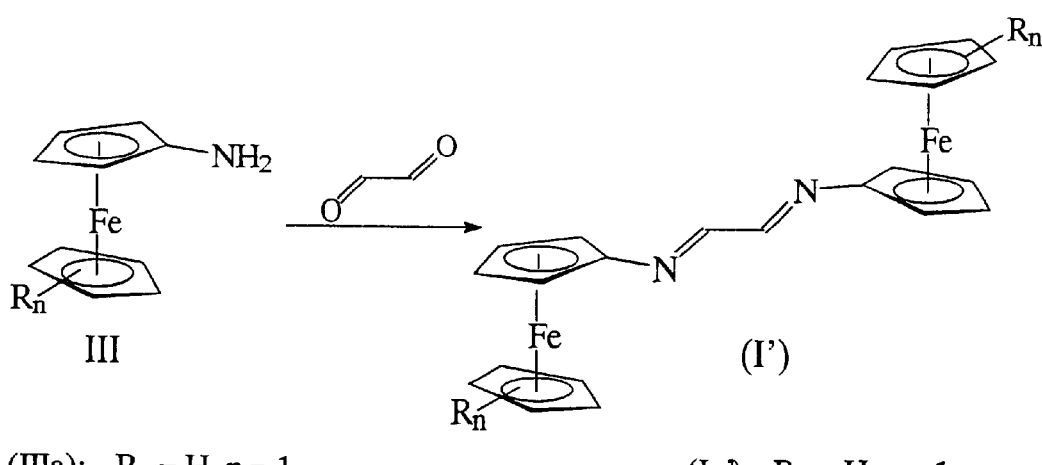
Figure 4:
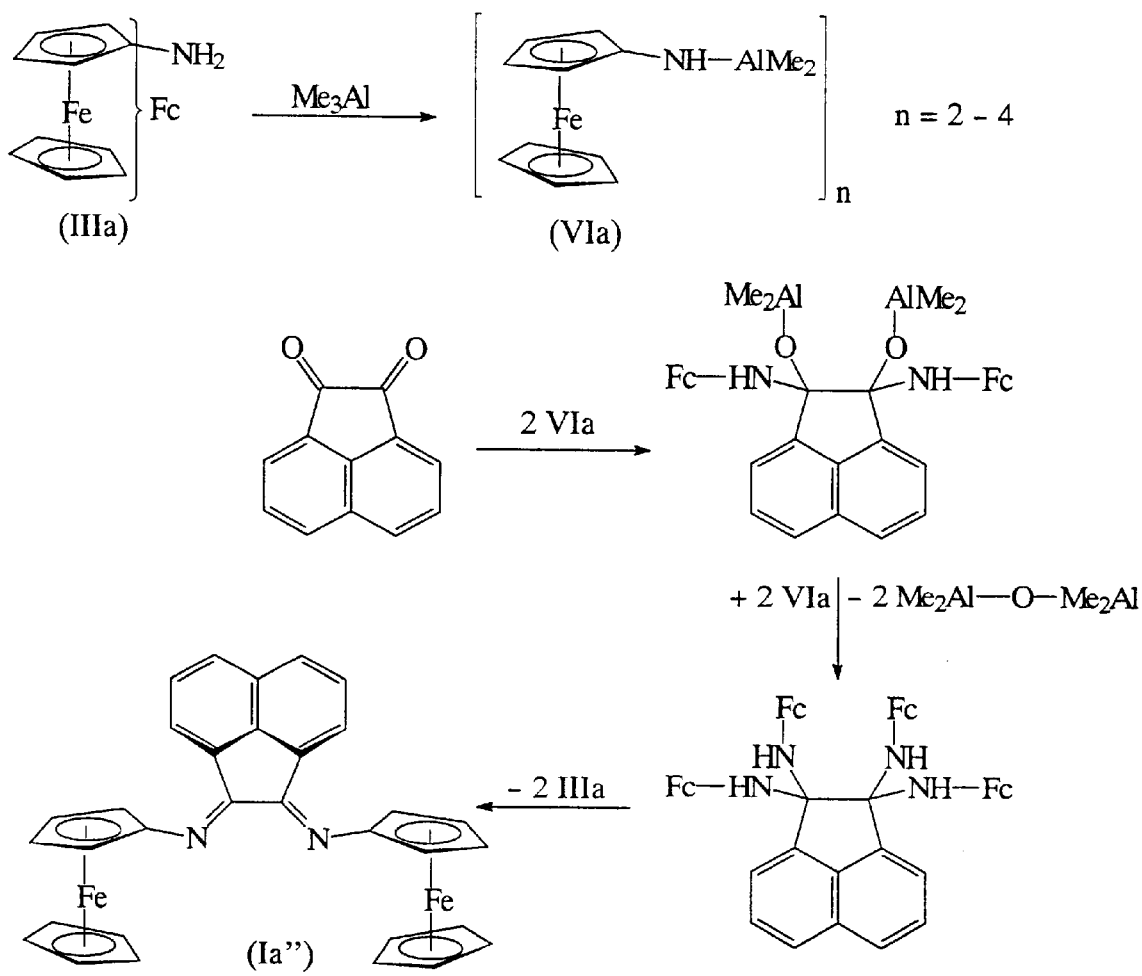

B Reaction of the Activated Amine with a 1,2-Dicarbonyl Compound:

A 1,2-dicarbonyl compound of the formula IV is added to the reaction mixture obtained as described in A. The molar ratio of the 1,2-dicarbonyl compound and the primary amine used is generally from 1:6 to 1:2, preferably from 1:4 to 1:2. The reaction temperature is generally, depending on the solvent and the reactants, from room temperature to 110° C., preferably from 50 to 110° C., particularly preferably from 70 to 110° C., and the reaction time is usually in the range from 30 minutes to 2 days, preferably from 5 hours to 24 hours, particularly preferably from 8 to 16 hours. The work-up is carried out in a customary fashion, e.g. by removal of the solvent under reduced pressure and subsequent purification of the resulting product by means of chromatography. FIGS. 3 and 4 show, in each case by way of example, the preparation of ferrocenyl-substituted 1,2-diimine compounds.

The process of the present invention makes it possible to prepare 1,2-diimine compounds which bear bulky radicals and can be obtained only with difficulty or not at all by other methods. The present invention therefore also provides for the use of trialkylaluminum compounds for preparing 1,2-diimine compounds from 1,2-dicarbonyl compounds and primary amines.

The process of the present invention or use of trialkylaluminum compounds according to the present invention makes it possible to obtain novel 1,2-diimine compounds which bear metallocenyl radicals on the imine nitrogen atoms. Accordingly, the present invention further provides compounds of the formula I,

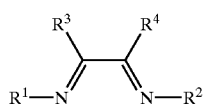 I where the symbols have the following meanings:
$R^3$, $R^4$ are, independently of one another, H, alkyl or aryl radicals, or
$R^3$ and $R^4$ are joined so as to form, with inclusion of the two imine carbon atoms, a 5- to 8-membered ring which may be saturated or unsaturated and may be unsubstituted or substituted by any hydrocarbon radicals,
and $R^1$ and $R^2$ are, independently of one another, metallocenyl radicals.

The compounds of the present invention are preferably prepared by the process of the present invention. In the compounds of the formula I, it is preferred that $R^3$ and $R^4$=H or $C_1$–$C_{20}$-alkyl or $R^3$ and $R^4$ are joined so as to form, with inclusion of the two imine carbon atoms, a 5- to 6-membered ring which may be saturated or unsaturated and may be unsubstituted or substituted by any hydrocarbon radicals. The metallocenyl radicals preferably contain a metal selected from the group consisting of Fe, $Co^+$, Ni, Ru, Os, $Rh^+$ and $Ir^+$. Particular preference is given to using Fe (ferrocenyl radicals).

The cyclopentadienyl radicals may be substituted or unsubstituted, and the metallocenyl units are bound to the imine nitrogen atom in the formula I via one of the two cyclopentadienyl radicals. Preferred substituents are —Me, —SiMe$_3$ or —SicHexMe$_2$.

Particular preference is given to compounds of the formulae Ia, Ib and Ic,

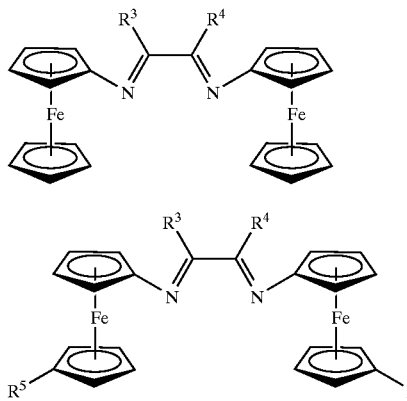
(Ia)

(Ib)
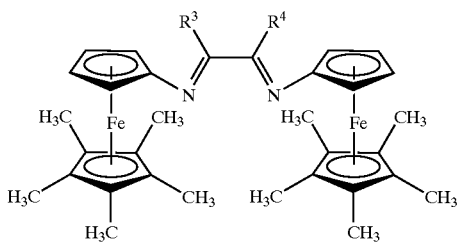

where R$^5$=—SiMe$_3$ (Ib$_1$) or —SicHexMe$_2$ (Ib$_2$);

(Ic)
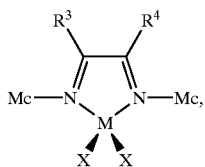

The compounds of the present invention are suitable as ligands for catalysts which can be used for the polymerization of unsaturated compounds. In particular, the compounds of the present invention are suitable as ligands for catalysts containing a metal of the late transition metals, i.e. a metal of transition group VIII of the Periodic Table of the Elements. The present invention therefore also provides compounds of the formula VII, (VII)

where
R$^3$ and R$^4$ are, independently of one another, H, alkyl or aryl radicals, or
R$^3$ and R$^4$ are joined so as to form, with inclusion of the two imine carbon atoms, a 5- to 8-membered ring which may be saturated or unsaturated and may be unsubstituted or substituted by any hydrocarbon radicals;
Mc is a metallocenyl radical which may be unsubstituted or substituted on the cyclopentadienyl radical,
M is a transition metal of transition group VIII of the Periodic Table of the Elements, and
X is halide or a C$_1$–C$_{20}$-alkyl radical.

Preferred radicals R$^3$, R$^4$ and metallocenyl (Mc) have been described above.

The transition metal M of transition group VIII of the Periodic Table of the Elements is preferably Pd, Co, Ni or Fe. Particular preference is given to Pd and Ni. The ligands X can be, independently of one another, halide or alkyl radicals. Preference is given to chloride, bromide or methyl radicals. The group MX$_2$ is particularly preferably PdCl$_2$, Pd(Cl)CH$_3$, NiCl$_2$, CoCl$_2$, NiBr$_2$ or FeCl$_2$.

Very particular preference is given to compounds of the formulae VIIa, VIIb and VIIc.

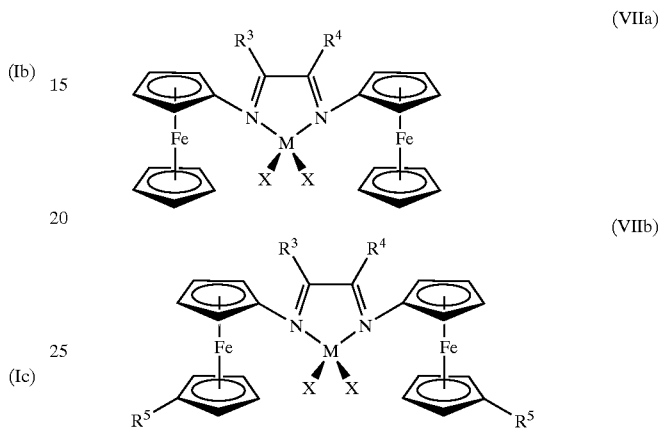

(VIIa)

(VIIb)

where R$^5$=—SiMe$_3$ (VIIb$_1$) or —SicHexMe$_2$ (VIIb$_2$);

(VIIc)
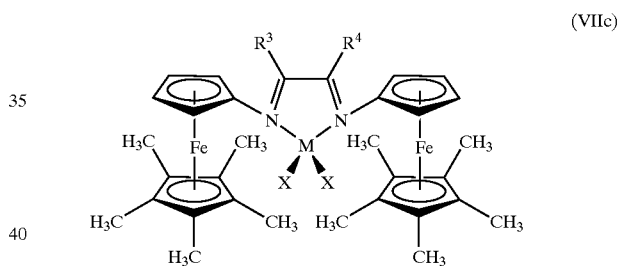

The novel compounds of the formula VII are usually prepared by reacting the corresponding compounds of the formula I with salts of metals of transition group VIII of the Periodic Table of the Elements.

In a preferred embodiment, a compound of the formula I which is suitable as ligand is mixed with an appropriate metal salt, e.g. NiCl$_2$(DME) (DME=1,2-dimethoxyethane), NiBr$_2$(DME)$_2$, CoCl$_2$, PdCl$_2$(benzonitrile)$_2$, PdClMe(COD) (COD=1,5-cyclooctadiene) in an organic solvent, e.g. tetrahydrofuran (THF) or methylene chloride. The molar ratio of ligand to metal salt is generally from 1.5:1 to 1:1.5, preferably from 1.2:1 to 1:1.2, particularly preferably about 1:1. The reaction mixture is stirred at temperatures of generally from room temperature to 50° C., preferably from room temperature to 40[000c]C., particularly preferably at room temperature, for generally from 0.5 hour to 16 hours, preferably from 1 to 6 hours, particularly preferably from 1 to 3 hours. The work-up is carried out in the customary fashion, e.g. by removal of the solvent under reduced pressure, washing of the residue with a solvent in which the residue (product) is largely insoluble, e.g. with diethyl ether, if appropriate digestion in a nonpolar solvent, e.g. hexane, filtration, washing and drying.

Figure 5:
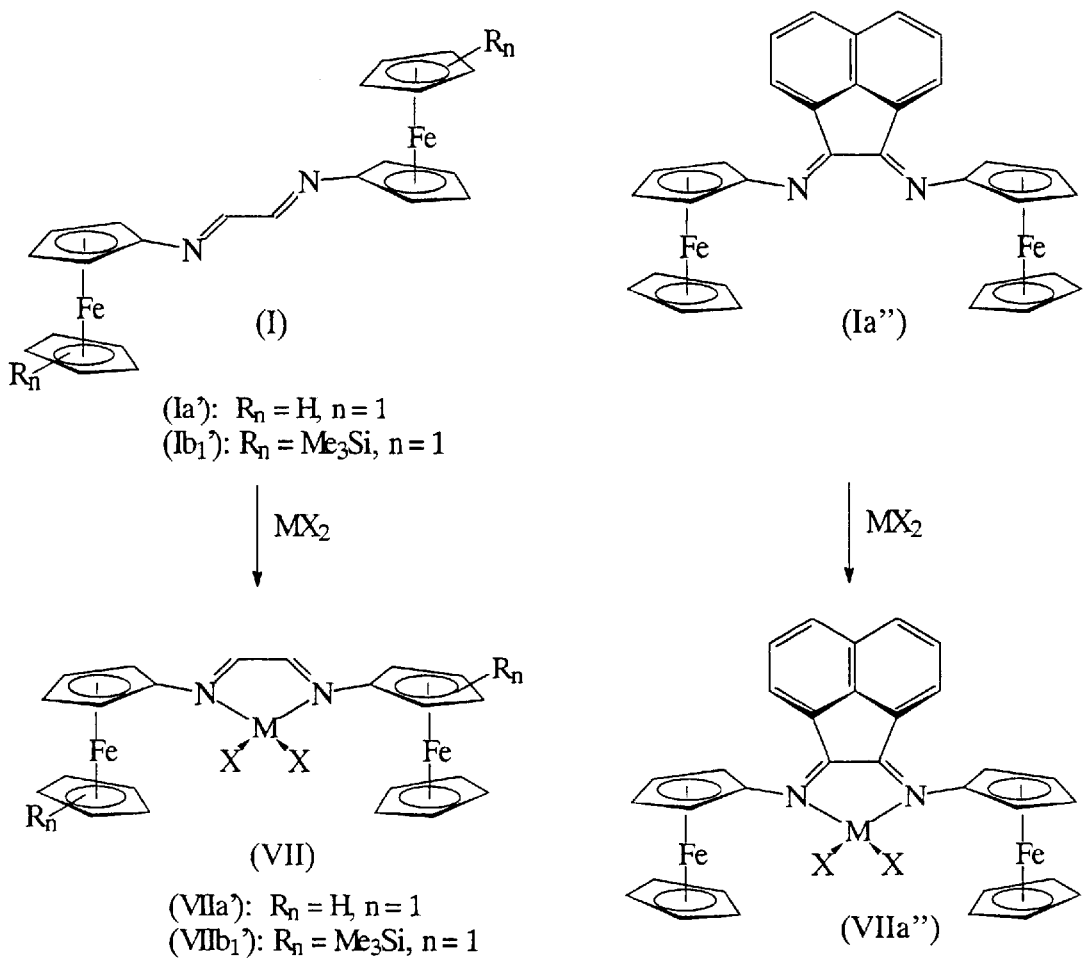

FIG. 5 shows, by way of example, the preparation of the metal complexes of the present invention. In the figure:

VII metal complex
I diazabutadiene
$MX_2$ metal salt

The novel metal complexes of the formula VII are suitable as catalysts for the polymerization of unsaturated compounds. Accordingly, the present invention further provides for the use of compounds of the formula VII as catalysts in a process for the polymerization of unsaturated compounds, and provides a process for preparing polyolefins by polymerization of unsaturated compounds in the presence of the catalyst according to the present invention and an activator.

It is known that the structures of polymers and thus also their properties and applications depend on the catalyst used in the polymerization and on the reaction conditions during the polymerization. The catalysts used according to the present invention thus provide a way of preparing novel polymers having specific property profiles.

Suitable activators (cocatalysts) are, in particular, strong, uncharged Lewis acids, ionic compounds having Lewis-acid cations and ionic compounds containing Brönsted acids as cations.

As strong, uncharged Lewis acids, preference is given to compounds of the formula VIII, $$M'X^1X^2X^3 \qquad (VIII)$$

where the symbols have the following meanings:
M' is an element of main group III of the Periodic Table of the Elements, preferably B, Al or Ga, particularly preferably B,
$X^1$, $X^2$, $X^3$ are each, independently of one another, hydrogen, $C_1$–$C_{10}$-alkyl, $C_6$–$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, preferably a haloaryl, particularly preferably pentafluorophenyl.

Very particular preference is given to compounds of the formula VIII in which $X^1$, $X^2$, $X^3$ are identical, preferably tris(pentafluorophenyl)borane.

Suitable ionic compounds having Lewis-acid cations are compounds of the formula IX, $$[(Y^{a+})Q_1Q_2 \ldots Q_z]^{d+} \qquad (IX)$$

where the symbols have the following meanings:
Y is an element of main groups I to VI or transition groups I to VIII of the Periodic Table of the Elements,
$Q_1$ to $Q_2$ are singly negatively charged radicals such as $C_1$–$C_{28}$-alkyl, $C_6$–$C_{15}$-aryl, alkylaryl, arylalkyl, haloalkyl, haloaryl each having from 6 to 20 carbon atoms in the aryl radical and from 1 to 28 carbon atoms in the alkyl radical, $C_1$–$C_{10}$-cycloalkyl, which may be unsubstituted or bear $C_1$–$C_{10}$-alkyl groups as substituents, halide, $C_1$–$C_{28}$-alkoxy, $C_6$–$C_{15}$-aryloxy, silyl or mercapto groups,
a is an integer from 1 to 6,
z is an integer from 0 to 5,
d is the difference a–z, but d is greater than or equal to 1.

Particularly useful Lewis-acid cations are carbonium cations, oxonium cations and sulfonium cations and cationic transition metal complexes. Particular mention may be made of the triphenylmethyl cation, the silver cation and the 1,1'-dimethylferrocenyl cation. They preferably have non-coordinating counterions, in particular boron compounds as are also mentioned in WO 91/09882, preferably tetrakis-(pentafluorophenyl)borate.

Ionic compounds containing Brönsted acids as cation and preferably likewise noncoordinating counterions are mentioned in WO 91/09882, the preferred cation is N,N-dimethylanilinium.

The amount of activator is preferably from 0.1 to 10 equivalents, based on the catalyst VII.

The polymerization process of the present invention is suitable for preparing homopolymers or copolymers. Unsaturated compounds or combinations of unsaturated compounds which are preferably used are unsaturated compounds selected from the group consisting of ethylene, $C_3$–$C_{20}$-monoolefins, ethylene and $C_3$–$C_{20}$-monoolefins, cycloolefins, cycloolefins and ethylene and cycloolefins and propylene. Preferred cycloolefins are norbornene, norbornadiene and cyclopentene.

When a catalyst according to the invention containing Pd(II) as central metal M is used, the abovementioned monomers can be copolymerized with monomers containing a carbonyl group, e.g. esters, carboxylic acids, carbon monoxide and vinyl ketones. The following combinations of unsaturated compounds are preferred: ethylene, $C_3$–$C_{20}$-monoolefins, ethylene and $C_3$–$C_{20}$-monoolefins, ethylene and an alkyl acrylate, in particular methyl acrylate, ethylene and an acrylic acid, ethylene and carbon monoxide, ethylene, carbon monoxide and an acrylate ester or an acrylic acid, in particular methyl acrylate, and also propylene and alkyl acrylate, in particular methyl acrylate.

The process of the present invention is particularly preferably used to prepare a polyethylene homopolymer, i.e. particular preference is given to using ethylene as unsaturated compound.

Depending on the reaction conditions and the monomers used, it is possible to obtain homopolymers, random copolymers or block copolymers by means of the process of the present invention.

The polymerization is carried out under generally customary conditions in solution, in suspension or in the gas phase. A polymerization in solution is preferred.

The catalyst systems used according to the present invention can be employed in the form of all-active catalysts or as supported catalysts, depending on the polymerization conditions.

As support materials, preference is given to using finely divided solids whose particle diameter is generally in the range from 1 to 200 μm, preferably from 30 to 70 μm.

Suitable support materials are, for example, silica gels, preferably those of the formula $SiO_2.Al_2O_3$, where a is from 0 to 2, preferably from 0 to 0.5; these are accordingly aluminosilicates or silicon dioxide. Such products are commercially available, for example Silica Gel 332 from Grace or ES 70x from Crosfield.

To remove adsorbed water, these support materials can be subjected to a thermal or chemical treatment or be calcined, with preference being given to carrying out a treatment at from 80 to 200° C., particularly preferably from 100 to 150° C.

Other inorganic compounds such as $Al_2O_3$ or $MgCl_2$ or mixtures in which these compounds are present can likewise be used as support materials.

Suitable solvents are, in particular, aprotic organic solvents. The catalyst system, the monomer or monomers and the polymer may be soluble or insoluble in the solvents, but the solvents should not participate in the polymerization. Suitable solvents are alkanes, cycloalkanes, selected halogenated hydrocarbons and aromatic hydrocarbons. Preferred solvents are hexane, toluene and benzene; particular preference is given to toluene.

The polymerization temperatures in a solution polymerization are generally in the range from −20 to 350° C., preferably from 0 to 100° C., particularly preferably from room temperature to 80° C. The reaction pressure is generally from 0.1 to 3000 bar, preferably from 1 to 200 bar, particularly preferably from 1 to 40 bar. The polymerization can be carried out in any apparatus suitable for the polymerization of unsaturated compounds.

The polymerization process of the present invention opens a route to polyolefins having novel structures and properties. Accordingly, the present invention also provides polymers which can be prepared by the process of the present invention.

The following examples illustrate the invention.

EXAMPLES

1. List of Compounds Prepared
1,2-Diimine Ligands:

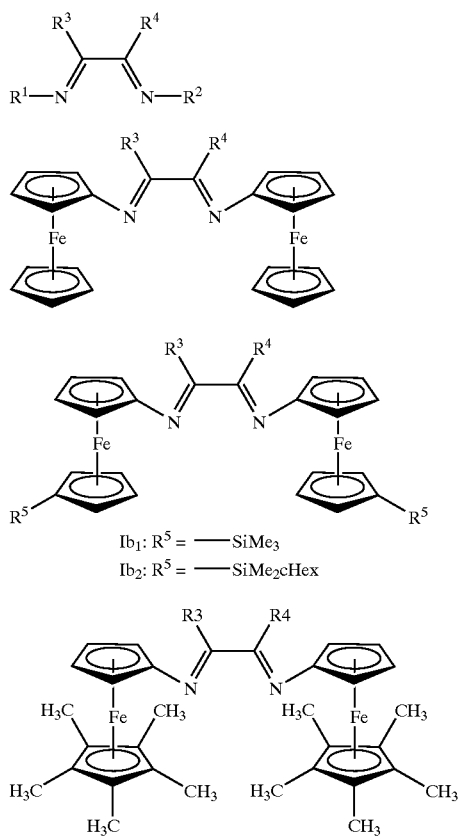

Numbering of the ligands having different radicals $R^3$ and $R^4$:

Ia', $Ib_1$', $Ib_2$', Ic': $R^3$ and $R^4$ are each H
Ia", Ib1", $Ib_2$", Ic": $R^3$ and $R^4$ together:=

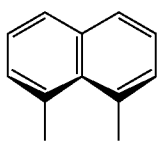

Amines

(IIIa)

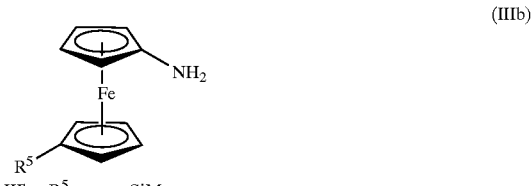

(IIIb)

$IIIb_1$: $R^5 =$ —SiMe₃
$IIIb_2$: $R^5 =$ —SiMe₂cHex

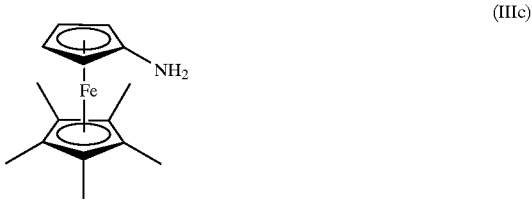

(IIIc)

Metal complexes:

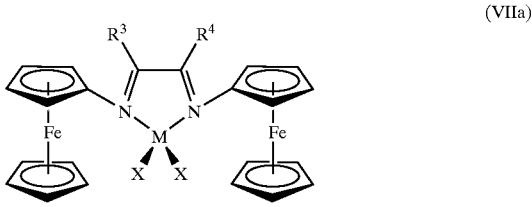

(VIIa)

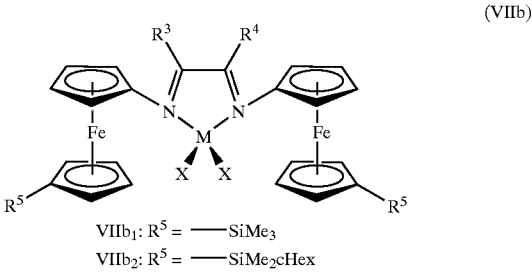

(VIIb)

$VIIb_1$: $R^5 =$ —SiMe₃
$VIIb_2$: $R^5 =$ —SiMe₂cHex

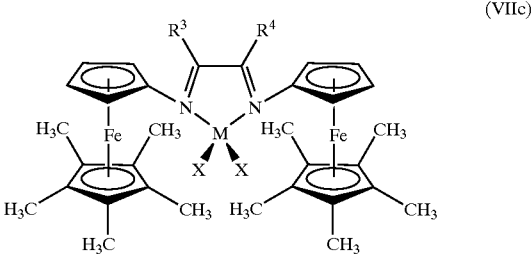

(VIIc)

Numbering of the metal complexes having different radicals $R^3$ and $R^4$:

VIIa', VIIb1', $VIIb_2$', VIIc': $R^3$ and $R^4$ are each H

VIIa", VIIb1", VIIb$_2$", VIIc": R$^3$ and R$^4$ together:=

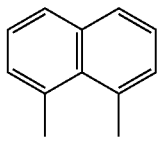

Numbering of the metal complexes with different radicals R$^3$ and R$^4$ and different metals, taking the complex VIIb$_1$' as an example:

| MX$_2$ | PdCl2 | Pd(Cl)CH3 | NiCl2 | CoCl2 | NiBr2 |
|---|---|---|---|---|---|
| Metal complex[1] | VIIb1'$_a$ | VIIb1'$_b$ | VIIa'c[2] | VIIb1'$_d$ | VIIb1'$_e$ |

1) Numbering of the complexes VII using the complex VIIb$_1$' as an example;
2) Numbering of the complexes VII using the complex VIIa' as an example, since this complex of the ligand VIIb$_1$' was not prepared.

2. Syntheses of Ligands and Complexes

The syntheses of ligands and complexes were carried out in the absence of air and moisture. The apparatuses and reagents used were prepared accordingly.

Syntheses of Ligands

1-Acetamido-1'-substituted Ferrocenes

N-(1'-Trimethylsilylferrocenyl)trimethylsilyacetamide: 4 ml (6 mmol) of t-butyllithium are added dropwise at −80° C. to a solution of 0.5 g (2.1 mmol) of monoferrocenylacetamide in 40 ml of THF. The mixture is subsequently warmed slowly to room temperature. After stirring for one hour at room temperature, an excess of trimethylchlorosilane is added [1.3 ml (10 mmol) of trimethylchlorosilane]. The mixture is poured into 100 ml of water and extracted a number of times with ether, and the combined ether phases are washed with water. Purification is carried out by means of column chromatography (eluant CH$_2$Cl$_2$; Al$_2$O$_3$).

Yield:
N-(1'-Trimethylsilylferrocenyl)trimethylsilyacetamide: 621 mg (1.6 mmol, 76% of theory)

Data for N-(1'-trimethylsilylferrocenyl)trimethylsilyacetamide: yellow crystals, m.p.: 145° C., C$_{18}$H$_{29}$FeNOSi$_2$, $^1$H-NMR(CDCl$_3$): δ 0.15 (s, 9H, SiMe$_3$), 0.20 (s, 9H, SiMe$_3$), 1.82 (s, 3H, CH$_3$), 3.91 (m, 2H, cp$_{subst}$) (cp=cyclopentadienyl), 4.05 (m, 2H, cp$_{subst}$), 4.30 (m, 2H, cp$_{subst}$) 4.49 (m, 2H, cp$_{subst}$)

N-[1'-(Dimethylcyclohexyl)silylferrocenyl]acetamide:

15.5 ml (25.2 mmol) of t-butyllithium are added dropwise at −80° C. to a solution of 2 g (8.4 mmol) of monoferrocenylacetamide in 40 ml of THF. The mixture is subsequently warmed slowly to room temperqture. After stirring for one hour at room temperature, an excess of cyclohexyldimethylchlorosilane is added [5 ml (23 mmol) of cyclohexyldimethylchlorosilane]. The mixture is poured into 100 ml of water and extracted a number of times with ether, and the combined ether phases are washed with water. Purification is carried out by means of column chromatography (eluant CH$_2$Cl$_2$; Al$_2$O$_3$).

Yield:
N-[1-(Dimethylcyclohexyl)silylferrocenyl]acetamide: 1.394 g (2.7 mmol, 32% of theory)

Data for N-[1'-(dimethylcyclohexyl)silylferrocenyl] acetamide: yellow oil, C$_{28}$H$_{43}$FeNOSi$_2$, $^1$H-NMR(CDCl$_3$): δ 0.05 (s, 6H, SiMe$_2$), 0.50–2.00(m, 11H, cHex), 2.00 (s, 3H, CH$_3$), 3.94(m, 2H, cp$_{subst}$), 4.03 (m, 2H, cpsubst), 4.30 (m, 2H, cpsubst), 4.53 (m, 2H, cp$_{subst}$), 6.80 (s, 1H, N—H).

1',2',3',4',5'-Pentamethylferrocene-1-carboxylic Acid Azide:

0.97 g (3.24 mmol) of 1',2',3',4',5'-pentamethylferrocene-1-carboxylic acid is converted into the acid chloride by reaction with 0.683 g (3.28 mmol) of phosphorus pentachloride in 30 ml of toluene, as described by B. Bildstein, A. Hradsky, H. Kopacka, R. Malleier, K. H. Ongania, *J. of Organomet. Chem.* 540 (1997) 127. After stirring for six hours, toluene, phosphorus oxytrichloride and the other volatile constituents are taken off in a high vacuum. The resulting residue is dissolved in 30 ml of absolute toluene and reacted with 0.21 g (3.24 mmol) of sodium azide in the presence of 0.737 g (3.24 mmol) of benzyltriethylammonium bromide as phase transfer catalyst to form 1',2',3',4',5'-pentamethylferrocene-1-carboxylic acid azide. After stirring overnight, an aqueous work-up is carried out and the product is chromatographed (Al$_2$O$_3$, eluant: petroleum ether/ether 1:1). In addition to 0.13 g of 1',2',3',4',5'-pentamethylferrocene-1-carboxylic acid azide, 0,2 g of 1',2', 3',4',5'-pentamethylferrocene-1-carboxylic acid is recovered, corresponding to a conversion of 0.77 g (2.56 mmol) of carboxylic acid into 0.13 g of acid azide in a yield of 15.6%.

Data for 1',2',3',4',5'-pentamethylferrocene-1-carboxylic acid azide: red crystals, C$_{16}$H$_{19}$FeN$_3$O, $^1$H-NMR(CDCl$_3$): δ 1.23 (s, 15H, cp*) (cp*=1',2',3',41,5'-pentamethylcyclopentadienyl), 4.53 (m, 2H, cp) (cp=cyclopentadienyl), 4.87 (m, 2H, cp).

1',2',3',4',5'-Pentamethylferrocen-1-yl-acetamide:

0.13 g (0.4 mmol) of 1',2',3',4',5'-pentamethylferrocene-1-carboxylic acid azide are stirred with 0.5 ml of acetic acid in 10 ml of acetic anhydride at 80° c for five hours. Aqueous work-up gives 0.102 g of 1',2',3',4',5-pentamethylferrocen-1-yl-acetamide.

Yield: 0.102 g (0.33 mmol, 82.5% of theory)

Data for 1',2',31',4',5'-pentamethylferrocen-1-yl-acetamide: orange crystals, m.p.: 149° C., C$_{17}$H$_{23}$FeNO, $^1$H-NMR(CDCl$_3$): δ 1.86 (s, 15H, cp*), 1.97 (s, 3H, CH$_3$), 3.63 (m, 2H, cp), 4.13 (m, 2H, cp).

Aminoferrocenes, IIIa, IIIb$_1$, IIIb$_2$, IIIc

Aminoferrocene

Aminoferrocene IIIa was prepared as described by M. Herberhold, M. Ellinger, L. Haumeier, in *Organometallic Synthesis* 3, R. B. King and J. J. Eisch (Editors), Elsevier, Amsterdam (1986) 81 and G. R. Knox, P. L. Pauson, D. Willison, E. Solcanioca, S. Toma, *Organometallics* 9 (1990) 301 (and references cited therein).

Aminoferrocenes IIIb$_1$, IIIb$_2$, IIIc, General Method:

The corresponding acetamide is added to a solution of potassium hydroxide in 50 ml of ethanol and the mixture is subsequently refluxed overnight. The product is poured into water, extracted a number of times with ether and the combined ether phases are washed with water, dried and evaporated on a rotary evaporator. Table 1 shows the data corresponding to the aminoferrocenes IIIb$_1$, IIIb$_2$, IIIc.

TABLE 1

| Amino-ferrocene | Acetamide | Amount of acetamide | Amount of KOH | Yield |
|---|---|---|---|---|
| IIIb$_1$ | N-(1'-Trimethylsilylferrocenyl)trimethylsilyl-acetamide | 0.45 g (1.2 mmol) | 2.5 g | 0.315 g, 99% |
| IIIb$_2$ | N-(1'-[Dimethylcyclohexyl)silylferrocenyl]-acetamide | 1.394 g (2.7 mmol) | 7 g | 0.827 g, 91% |
| IIIc | 1',2',3',4',5'-Pentamethylferrocen-1-yl-acetamide | 0.102 g (0.33 mmol) | 0.3 g | 87 mg, 97% |

Data for IIIb$_1$ (1-amino-1'-trimethylsilylferrocene): yellow oil, C$_{13}$H$_{19}$FeNSi, $^1$H-NMR(CDCl$_3$): δ 0.22 (s, 9H, SiMe$_3$), 2.54 (s, 2H, N—H), 3.77 (m, 2H, cp$_{subst}$), 3.92 (m, 2H, cp$_{subst}$), 3.98 (m, 2H, cp$_{subst}$), 4.24 (m, 2H, cp$_{subst}$).

Data for IIIb$_2$ (1-amino-1'-dimethylcyclohexylferrocene): yellow oil, C$_{18}$H$_{27}$FeNSi, $^1$H-NMR(CDCl$_3$): δ 0.22 (s, 9H, SiMe$_3$), 0.5–2.0 (m, 11H, cHex), 2.37 (s, 2H, N-H), 3.75 (m, 2H, cp$_{subst}$), 3.91 (m, 4H, 2*cp$_{subst}$), 4.21 (m, 2H, cp$_{subst}$).

Data for IIIc (1-amino-1',2',3',4',5'-pentamethylferrocene): brownish yellow, unstable oil, C$_{15}$H$_2$FeN, IR(KBr): (cm$^{-1}$) 3411m, 2964m, 2927m, 2875m, 1701w, 1638w, 1618w, 1493w, 1452w, 1379m, 1261m, 1094m, 1032m, 866w, 802s, 480w. MS (EI, 70 eV): m/z(%) 271 (100) (M$^+$), 133.5 (100) (cp*), 121 (16) (Fecp$^+$).

1,4-Diferrocenyldiazabutadienes Ia', Ib$_1$', Ib$_2$', Ic':

The corresponding ferrocenylamine is dissolved in 40 ml of acetone and 20 ml of water and subsequently admixed with an excess of 40% strength aqueous glyoxal solution. After stirring overnight at room temperature, the violet product is precipitated completely by addition of 200 ml of water and is subsequently filtered off. For further purification, it is washed a number of times with water and dried in a high vacuum. Table 2 shows the data corresponding to the 1,4-diferrocenyldiazabutadienes Ia', Ib$_1$', Ib$_2$', Ic'.

TABLE 2

| 1,4-Diferrocenyl-diazabutadiene | Amino-ferrocene | Amount of aminoferrocene | Amount of glyoxal | Yield |
|---|---|---|---|---|
| Ia' | IIIa | 0.86 g (4.3 mmol) | 0.3 g (2.1 mmol) | 0.86 g, 94.8% |
| Ib$_1$' | IIIb$_1$ | 0.68 g (2.2 mmol) | 0.16 g (1.1 mmol) | 0.54 g, 76.3% |
| Ib$_2$' | IIIb$_2$ | 0.827 g (2.4 mmol) | 0.175 g (1.2 mmol) | 0.64 g, 60% |
| Ic' | IIIc | 38 mg (0.14 mmol) | 10 mg (0.07 mmol) | 38 mg, 95.7% |

Data for Ia': violet crystals, m.p.: decomp. above 200° C., C$_{22}$H$_{20}$Fe$_2$N$_2$, $^1$H-NMR(CD$_2$Cl$_2$): δ 4.19 (s, 10H, cp$_{unsubst}$), 4.38 (m, 4H, cp$_{subst}$), 4.63 (m, 4H, cp$_{subst}$), 8.33 (s, 2H, imine).

Data for Ib$_1$': violet crystals, m.p.: decomp. above 200°, C$_{28}$H$_{36}$Fe$_2$N$_2$Si$_2$, $^1$H-NMR(CDCl$_3$): δ 0.20 (s, 18H, SiMe$_3$), 4.10 (m, 4H, cp$_{subst}$), 4–34 (m, 4H, cp$_{subst}$), 4.36 (m, 4H, cp$_{subst}$), 4.59 (m, 4H, cp$_{subst}$), 8.32 (s, 2H, imine).

Data for Ib$_2$': violet crystals, m.p.: decomp. above 200°, C$_{38}$H$_{52}$Fe$_2$N$_2$Si$_2$, $^1$H-NMR(CDCl$_3$): δ 0.18 (s, 6H, SiMe$_2$), 0.50–2.00 (m, 11H, cHex), 4.05 (m, 4H, cp$_{subst}$), 4.34 (m, 4H, cp$_{subst}$), 4.36 (m, 4H, cp$_{subst}$), 4.58 (m, 4H, cp$_{subst}$), 8.32 (s, 2H, imine).

Data for Ic': violet crystals, C$_{32}$H$_{40}$Fe$_2$N$_2$, m.p.: decomp. above 90° C., $^1$H-NMR(CD$_2$Cl$_2$): δ 1.82 (s, 30H, 10×CH$_3$), 4.18 (m, 4H, C$_{3,3',4,4'}$H), 4.21 (m, 4H, C$_{2,2',5,5'}$H), 7.55 (m, 1H, imine), 7.70 (m, 1H, imine).

bis(Ferrocenylimino)acenaphthene Ia":

0.467 g (2.32 mmol) of aminoferrocene IIIa are stirred together with 1.16 ml (2.32 mmol) of trimethylaluminum (2 molar in toluene) in 50 ml of absolute toluene for three hours at 70° C. using a method analogous to that of B.Bildstein, P. Denifl *Synthesis* (1994) 158. Without cooling the mixture, 0.105 g (0.58 mmol) of acenaphthenequinone is subsequently added thereto and the mixture is stirred overnight at 110° C. The solvent is taken off in a high vacuum and the constituents of the brownish red residue are separated by chromatography (basic Al$_2$O$_3$, eluant: petroleum ether/ether=1:1).

Yield: 0.230 mg (0.42 mmol, 72.3 % of theory)

Data for bis(ferrocenylimino)acenaphthene Ia": blue crystals, C$_{32}$H$_{24}$Cl$_2$COFe$_2$N$_2$, m.p.: decomp. above 150° C., $^1$H-NMR(CD$_2$Cl$_2$): δ 4.23–4.53 (m, 18H, ferrocenyl), 7.39–7.90 (m, 6H, acenaphthene-H).

Preparation of the Metal Complexes (General Method):

One molar equivalent of ligand is mixed with one molar equivalent of the respective metal salt (NiCl$_2$ (DME), NiBr$_2$ (DME)$_2$, CoCl$_2$, PdCl$_2$ (benzonitrile)$_2$, Pd(COD)ClMe) in tetrahydrofuran or methylene chloride at room temperature and the mixture is stirred for two hours. The solvent is taken off on a rotary evaporator and the green solid is digested with ether, filtered off and washed with ether. In the case of Pd(COD)ClMe, the product has to be digested once more with hexane to obtain an amorphous, dark green solid. Table 3 shows the data corresponding to the metal complexes VIIa'$_a$, VIIa'$_b$, VIIa'$_c$, VIIa'$_d$, VIIb$_{1'a}$, VIIb$_{1'b}$, VIIb$_{1'e}$, VIIb$_{1'd}$, VIIa"$_a$, VIIa"$_b$, VIIa"$_c$, VIIa"$_d$.

TABLE 3

| Metal complex | Diazabutadiene | Metal salt (MX$_2$) | Yield |
|---|---|---|---|
| VIIa'$_a$ | Ia' | PdCl$_2$ | 64.0% |
| VIIa'$_b$ | Ia' | Pd(Cl)CH$_3$ | 80.0% |
| VIIa'$_c$ | Ia' | NiCl$_2$ | 98.0% |
| VIIa'$_d$ | Ia' | CoCl$_2$ | 82.5% |
| VIIb$_{1'a}$ | Ib$_1$' | PdCl$_2$ | 81.4% |
| VIIb$_{1'b}$ | Ib$_1$' | Pd(Cl)CH$_3$ | 60.7% |
| VIIb$_{1'e}$ | Ib$_1$' | NiBr$_2$ | 66.0% |
| VIIb$_{1'd}$ | Ib$_1$' | CoCl$_2$ | 68.1% |

TABLE 3-continued

| Metal complex | Diazabutadiene | Metal salt (MX$_2$) | Yield |
|---|---|---|---|
| VIIa"$_a$ | Ia" | PdCl$_2$ | 91.3% |
| VIIa"$_b$ | Ia" | Pd(Cl)CH$_3$ | 70.0% |
| VIIa"$_c$ | Ia" | NiCl$_2$ | 85.8% |
| VIIa"$_d$ | Ia" | CoCl$_2$ | 77.2% |

Data for VIIa'$_a$: green crystals, C$_{22}$H$_{20}$Cl$_2$CoFe$_2$N$_2$Pd, m.p.: <300° C., IR(KBr): (cm$^{-1}$) 3091w, 1624m, 1530s, 1425s, 1412m, 1375w, 1350w, 1238vs, 1169w, 1107s, 1032m, 1001m, 926w, 827s, 642w, 474s.

Data for VIIa'$_b$: green crystals, C$_{23}$H$_{23}$ClFe$_2$N$_2$Pd, m.p.: decomp. above 200° C., IR(KBr): (cm$^{-1}$) 3083w, 2963w, 2886w, 1634m, 15741m, 1429m, 1410m, 1375m, 1348m, 1234w, 1165w, 1107s, 1026s, 1001s, 924s, 889w, 818vs, 644w, 542w, 490vs, 470vs. MS(FAB): m/e(%) 582 (50) (M$^+$), 530 (100) (M$^+$−CH$_3$Cl). UV(CH$_2$Cl$_2$) $\lambda_{max}(\epsilon)$=371 nm (11000), 729 nm (4000).

Data for VIIa'$_c$: green crystals, C$_{22}$H$_{20}$Cl$_2$Fe$_2$NiN$_2$, m.p.: <300° C., IR(KBr): (cm$^{-1}$) 3083w, 1628m, 1574vs, 1472m, 1441s, 1410m, 1375w, 1369w, 1259m, 1105m, 1051w, 1038w, 1024w, 1001m, 960w, 874s, 818w, 798w, 520w, 486s, 461w. MS(FAB): m/e(%) 517 (100) (M$^+$−Cl), 482 (50) (M$^+$−2Cl). UV(CH$_2$Cl$_2$) $\lambda_{max}(\epsilon)$=411 nm (17000), 780 nm (8000).

Data for VIIa'$_d$: green crystals, C$_{22}$H$_{20}$Cl$_2$COFe$_2$N$_2$, m.p.: <300° C.; IR(KBr): (cm$^{-1}$) 3087w, 1645m, 1574vs, 1474w, 1439s, 1410m, 1385s, 1375m, 1259m, 1105m, 1049m, 1038m, 1020m, 1001s, 960w, 818vs, 798w, 648w, 519m, 493s, 486m, 461w. MS(FAB): m/e(%) 518 (100) (M$^+$−Cl). UV(CH$_2$Cl$_2$) $\lambda_{max}(\epsilon)$=416 nm (25000), 830 nm (13000).

Data for VIIb$_{1'a}$: green crystals, C$_{28}$H$_{36}$Cl$_2$Fe$_2$N$_2$Si$_2$Pd, m.p.: decomp. above 200° C.; IR(KBr): (cm$^{-1}$) 3087w, 2954m, 2896w, 1624w, 1533m, 1427m, 1406w, 1375w, 1364w, 1302w, 1248s, 1163s, 1038s, 924w, 901m, 877w, 837vs, 754m, 692w, 630w, 482w, 418w. UV(CH$_2$Cl$_2$) $\lambda_{max}(\epsilon)$=398.5 nm (12000), 846.5 nm (5000).

Data for VIIb$_{1'b}$: green crystals, C$_{29}$H$_{39}$ClFe$_2$N$_2$Si$_2$Pd, m.p.: decomp. above 200° C.; IR(KBr): (cm$^{-1}$) 3087w, 2954m, 2894w, 1632w, 1541m, 1427w, 1404m, 1383w, 1373w, 1364w, 1248s, 1163s, 1095w, 1036m, 924w, 901m, 874w, 837vs, 754w, 692w, 630w, 495w. MS(FAB): m/e(%) 673 (10) (M$^+$−CH$_3$, Cl), 568 (100) (M$^+$−PdCH$_3$Cl). UV(CH$_2$Cl$_2$) $\lambda_{max}$=376 nm (10000), 731nm (4000).

Data for VIIb$_{1'e}$: green crystals, C$_{28}$H$_{36}$Br$_2$Fe$_2$N$_2$Si$_2$Ni, m.p.: decomp. above 200° C.; IR(KBr): (cm$^{-1}$) 3077w, 2956m, 1634w, 1564s, 1470w, 1437m, 1375w, 1364w, 1250s, 1165m, 1053w, 1036m, 960m, 901m, 876w, 837vs, 818s, 754w, 630w, 522m, 492w, 476w. MS(FAB): m/e(%) 787 (20) (M$^+$), 707 (100) (M$^+$−B r), 626 (50) (M$^+$−2Br), 548 (70) (M$^+$−NiBr$_2$). UV(CH$_2$Cl$_2$) $\lambda_{max}(\epsilon)$=421 nm (13000), 807 nm (6000).

Data for VIIb$_{1'd}$: green crystals, C$_{28}$H$_{36}$COCl$_2$Fe$_2$N$_2$Si$_2$, m.p.: decomp. above 200° C., IR(KBr): (cm$^{-1}$) 2956m, 1628w, 1568s, 1472w, 1439m, 1375w, 1364w, 1250s, 1163s, 1051w, 1038m), 960w, 901m, 877m, 837vs, 754w, 646w, 630w, 520w, 497w, 474w. MS(FAB): m/e(%) 697 (7) (M$^+$), 662 (40) (M$^+$−Cl), 627 (7) (M$^+$−2Cl), 568 (100) (M$^+$−CoCl$_2$). UV(CH$_2$Cl$_2$) $\lambda_{max}(\epsilon)$=422.5 nm (11000), 846 nm (6000).

Data for VIIa"$_a$: green crystals, C$_{32}$H$_{24}$Cl$_2$Fe$_2$N$_2$Pd, m.p.: decomp. above 200° C., IR (KBr) (cm$^{-1}$) 1633s, 1612m, 1430w, 1262m, 1110m, 1082m, 1042m, 863m, 764m, MS(FAB) m/e (%)=691 (8) (M$^+$−Cl), 653 (15) (M$^+$−2 Cl), 549 (14) (M$^+$−PdCl$_2$). UV(CH$_2$Cl$_2$) $\lambda_{max}(\epsilon)$=312 nm (22000), 331 nm (22000), $^3$33 nm (22000), 836 nm (5000).

Data for VIIa"$_b$: green crystals C$_{33}$H$_{27}$ClFe$_2$N$_2$Pd, m.p.: decomp. above 170° C., IR (KBr) (cm$^{-1}$) 1719m, 1656m, 1630s, 1432m, 1420m, 1281m, 1262m, 1127m, 1106s, 1055s, 1028s, 1001s, 828 s, 780s. MS(FAB) m/e (%)=706 (23) (M$^+$+H), 669 (5) (M$^+$−Cl), 653 (80) (M$^+$−Cl, —Me), 548 (68) (M$^+$−PdClMe). UV(CH$_2$Cl$_2$) $\lambda_{max}(\epsilon)$=338 nm (13000), 684 nm (2000).

Data for VIIa"$_c$: green crystals, C$_{32}$H$_{24}$Cl$_2$Fe$_2$N$_2$Ni, m.p.: decomp. above 150° C., IR (KBr) (cm$^{-1}$)1630s, 1432w, 1262w, 1105m, 1042m, 1020m, 842m, 81 m. MS(FAB) m/e(%) 641 (22) (M$^+$−Cl), 606 (31) (M$^+$−2 Cl), 549 (18) (M$^+$−NiCl$_2$). UV(CH$_2$Cl$_2$) $\lambda_{max}(\epsilon)$=333 nm (7000), 729 nm (2000).

Data for VIIa"$_d$: green crystals, C$_{32}$H$_{24}$Cl$_2$COFe$_2$N$_2$, m.p.: decomp. above 200° C., IR (KBr) (cm$^{-1}$)1633s, 1430w, 1262w, 1110m, 1042w, 863m. MS(FAB) m/e(%)= 677 (4) (M$^+$), 642 (5) (M$^+$−Cl), 549 (4) (M$^+$−CoCl$_2$). UV(CH$_2$Cl$_2$) $\lambda_{max}(\epsilon)$=311 nm (7000), 345 nm (7000), 779 nm (2000).

FIGS. 1 to 5 show corresponding reaction schemes for preparing the compounds listed.

Homopolymerization of Ethene

Activation with MAO (Methylaluminoxane), Polymerization Example 1

140 ml of dry toluene are placed in a 250 ml four-neck glass flask. After addition of 12.4 ml (19 mmol) of MAO and 13.8 mg (19 μmol) of the catalyst VIIb$_{1'c}$, 40 l/h of ethene are blown through the solution under atmospheric pressure. The polymerization temperature is set to 50–55° C. After 4.5 hours, the polymerization is stopped by addition of HCl/MeOH. The mixture is separated in a separating funnel and the organic (toluene) phase is washed with H$_2$O and dried. After filtration through an aluminum oxide column (neutral), the polymer is separated off by evaporation of the toluene (75° C., 0.1 mbar, 3 h). Table 4, polymerization example 1, summarizes the data for the polyethylene obtained.

Cationic Activation, Polymerization Example 2

140 ml of dry toluene are placed in a 250 ml four-necked glass flask. After addition of 1.5 ml (3 mmol) of TIBAL (triisobutylaluminum) and 220 mg (0.3 mmol) of catalyst VIIb$_{1'b}$, the reaction mixture is stirred for 1 hour. 268 mg (about 0.333 mmol) of N,N-dimethylanilinium tetrakis (pentafluorophenyl)borate (DMAB) are then added and the mixture is stirred for another 30 minutes. 40 l/h of ethene are then blown through the solution under atmospheric pressure. The polymerization temperature is set to 50–55° C. After 5 hours, the polymerization is stopped by addition of HCl/MeOH. The mixture is separated in a separating funnel. The organic (toluene) phase is washed with H$_2$O and dried. After filtration through an aluminum oxide column (neutral), the polymer is separated off by evaporation of the toluene (75° C., 0.1 mbar, 3 h). Table 4, polymerization example 2, summarizes the data for the polyethylene obtained.

TABLE 4

| Polymerization example | Catalyst | Activator | Polymerization temperature, ° C. | $\eta^{1)}$ |
|---|---|---|---|---|
| 1 | VIIb$_{1'c}$ | MAO | 50–55 | 0.4 |
| 2 | VIIb$_{1'b}$ | DMAB | 50–55 | 0.3 |

[1] was determined in accordance with ISO 1628-3

We claim:

1. A process for preparing 1,2-diimine compounds of the formula

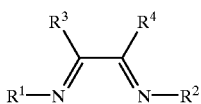

I where the symbols have the following meanings $R^1$ and $R^2$ are, independently of one another, alkyl, aryl or metallocenyl radicals, and $R^3$, $R^4$ are, independently of one another, H, alkyl or aryl radicals, or $R^3$ and $R^4$ are joined so as to form, with inclusion of the two imine carbon atoms, a 5- to 8-membered ring which may be saturated or unsaturated and may be unsubstituted or substituted by any hydrocarbon radicals, by reacting 1,2-dicarbonyl compounds with primary amines, which have been activated with trialkylaluminum compounds prior to the reaction with the 1,2-dicarbonyl compounds.

2. A process as claimed in claim 1, wherein the radicals $R^1$ and $R^2$ are, independently of one another, substituted aryl radicals or metallocenyl radicals.

3. A process as claimed in claim 2, wherein $R^1$ and $R^2$ are, independently of one another, metallocenyl radicals.

4. A process as claimed in claim 3, wherein $R^1$ and $R^2$ are ferrocenyl radicals.

5. A process as claimed in claim 4, wherein a ferrocenyl radical of the formula IIa, IIb or IIc,

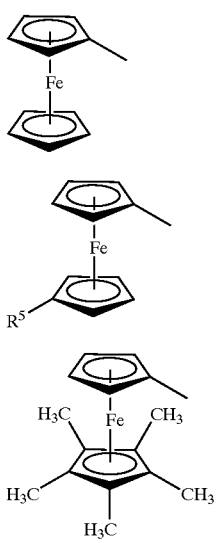

IIa

IIb

IIc where $R^5$ is —Me, —SiMe$_3$ or —SiHexMe$_2$ is used.

6. A process as claimed in claim 1, wherein 1,2-dicarbonyl compounds of the formula IV,

IV where the symbols have the following meanings:

$R^3$ and $R^4$ are, independently of one another, H, alkyl or aryl radicals, or $R^3$ and $R^4$ are joined so as to form, with inclusion of the two carbonyl carbon atoms, a 5- to 8-membered ring which may be saturated or unsaturated and may be unsubstituted or substituted by any hydrocarbon radicals, are used.

7. A process as claimed in claim 6, wherein 1,2-dicarbonyl compounds of the formula IVa, IVb, or IVc,

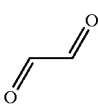

IVa

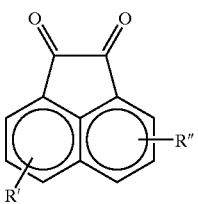

IVb

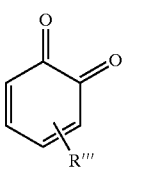

IVc

where R', R", R'" are each H, alkyl or aryl, are used.

8. A process as claimed in claim 1, wherein trialkylaluminum compounds of the formula V, $$R^6R^7R^8Al \qquad V$$

where $R^6$, $R^7$ and $R^8$ are each, independently of one another, $C_1$–$C_{10}$-alkyl, are used.

9. A process as claimed in claim 8, wherein $R^6$, $R^7$ and $R^8$ are each methyl.

10. A 1,2-diimine compound of the formula I as claimed in claim 1, wherein $R^1$ and $R^2$ are, independently of one another, metallocenyl radicals.

11. A compound as claimed in claim 10, wherein $R^1$ and $R^2$ are ferrocenyl radicals.

12. A compound of the formula VII,

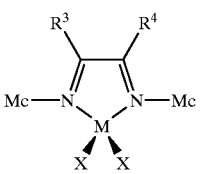

VII where the symbols have the following meanings:

$R^3$ and $R^4$ are, independently of one another, H, alkyl or aryl radicals, or $R^3$ and $R^4$ are joined so as to form, with inclusion of the two imine carbon atoms, a 5- to 8-membered ring which may be saturated or unsaturated and may be unsubstituted or substituted by any hydrocarbon radicals, and Mc is a metallocenyl radical which may be unsubstituted or substituted on the cyclopentadienyl radical, M is a transition metal of transition group VIII of the Periodic Table of the Elements, and X is a halide or a $C_1$–$C_{20}$-alkyl radical.

13. A process for preparing compounds of the formula VII as claimed in claim 12, by reacting corresponding compounds of the formula I

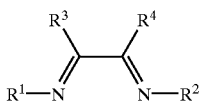

where the symbols have the following meanings $R^1$ and $R^2$ are, independently of one another, alkyl, aryl or metallocenyl radicals, and $R^3$, $R^4$ are, independently of one another, H, alkyl or aryl radicals, or $R^3$ and $R^4$ are joined so as to form, with inclusion of the two imine carbon atoms, a 5- to 8-membered ring which may be saturated or unsaturated and may be unsubstituted or substituted by any hydrocarbon radicals, with salts of metals of transition group VIII of the Periodic Table of the Elements.

14. A process for preparing polyolefins by polymerization of unsaturated compounds in the presence of an activator and a compound of the formula VII as claimed in claim 12 as catalyst.

15. A process as claimed in claim 14, wherein methylaluminoxane or N,N-dimethylanilinium tetrakis (pentafluorophenyl)borate is used as activator.

16. A process as claimed in claim 14, wherein an unsaturated compound or a combination of unsaturated compounds selected from the group consisting of ethylene, $C_3$–$C_{20}$-monoolefins, ethylene and $C_3$–$C_{20}$-monoolefins, cycloolefins, cycloolefins and ethylene and cycloolefins and propylene is used.

17. A process as claimed in claim 14, wherein, when using a catalyst of the formula VII with Pd(II) as central metal M, unsaturated compounds or combinations of unsaturated compounds selected from the group consisting of ethylene, $C_3$–$C_{20}$-monoolefins, ethylene and $C_3$–$C_{20}$-monoolefins, ethylene and an alkyl acrylate, ethylene and acrylic acid, ethylene and carbon monoxide, ethylene, carbon monoxide and an acrylate ester or an acrylic acid, propylene and an alkyl acrylate, cycloolefins, cycloolefins and ethylene and cycloolefins and propylene are used.

18. A process as claimed in claim 14, wherein ethylene is used as unsaturated compound.

19. A process as claimed in claim 14, wherein the polymerization is carried out at from 0 to 100° C.

20. A process as claimed in claim 14, wherein the polymerization is carried out at a pressure of from 0.1 to 3000 bar.

21. A polyolefin which can be prepared by a process as claimed in claim 14.

* * * * *